US009689827B2

(12) United States Patent
Pratt et al.

(10) Patent No.: US 9,689,827 B2
(45) Date of Patent: Jun. 27, 2017

(54) POTENTIOSTATIC CIRCUITS FOR ELECTROCHEMICAL SENSORS

(71) Applicant: Honeywell International Inc., Morristown, NJ (US)

(72) Inventors: Keith Francis Edwin Pratt, Portsmouth (GB); Martin Willett, Waterlooville (GB); Lei Xiao, London (GB); Ali Hosseinmardi, Portsmouth (GB)

(73) Assignee: Honeywell International Inc., Morris Plains, NJ (US)

( * ) Notice: Subject to any disclaimer, the term of this patent is extended or adjusted under 35 U.S.C. 154(b) by 601 days.

(21) Appl. No.: 14/049,426

(22) Filed: Oct. 9, 2013

(65) Prior Publication Data

US 2015/0096905 A1    Apr. 9, 2015

(51) Int. Cl.
G01N 27/28    (2006.01)
G01N 27/404    (2006.01)
G01N 27/49    (2006.01)

(52) U.S. Cl.
CPC ........... *G01N 27/28* (2013.01); *G01N 27/404* (2013.01); *G01N 27/49* (2013.01)

(58) Field of Classification Search
CPC .................. G01N 27/28; G01N 27/283; G01N 27/407–27/41
See application file for complete search history.

(56) References Cited

U.S. PATENT DOCUMENTS

| 5,902,467 | A | 5/1999 | Wang et al. |
| 6,758,962 | B1 | 7/2004 | Fitzgerald et al. |
| 2010/0252455 | A1* | 10/2010 | Pratt .................... G01N 33/007 205/793 |

FOREIGN PATENT DOCUMENTS

| CN | 2301723 Y | 12/1998 |
| DE | 19925921 A1 | 12/2000 |
| JP | 2006194708 A | 7/2006 |
| WO | 97/35186 A1 | 9/1997 |

OTHER PUBLICATIONS

Extended European search report for corresponding EP application 14185456.2, dated Feb. 6, 2015.
Eutech, Dissolved Oxygen, Internet URL: http://www.eutechinst.com/brochures/annual_catalogue/2012_catalogue_co.pdf, Jan. 1, 2012.
Ahmadi, Current-Mirror-Based Potentiostats for Three-Electrode Amperometric Electrochemical Sensors, IEEE Transactions on Circuits and Systems—1: Regular Papers, Jul. 2009, pp. 1339-1348, vol. 56, No. 7.
China Application No. 201410523464.0, Office Action, mailed Jul. 19, 2016, 17 pages.
China Patent Application No. 201410523464.0, Office Action, mailed Mar. 15, 2017, 7 pages.

* cited by examiner

*Primary Examiner* — J. Christopher Ball
(74) *Attorney, Agent, or Firm* — Conley Rose, P.C.; Kristin Jordan Harkins

(57) ABSTRACT

An electrochemical detector can be powered partly, or entirely by voltages generated by the sensor. Using either active circuits or a passive component which produces a predetermined voltage drop in the respective sensor, two electrode consumable anode oxygen sensors can be provided which do not evolve hydrogen during operation.

18 Claims, 4 Drawing Sheets

Implementation of zero power potentiostat where op amp can be powered directly by sensor Implementation of a temperature compensated diode bias circuit Implementation of a temperature compensated diode bias circuit, intended for use with the zinc sensor

POTENTIOSTATIC CIRCUITS FOR ELECTROCHEMICAL SENSORS

FIELD

The application pertains to circuits and methods of driving electrochemical sensors. More particularly, the application pertains to circuits which are powered partly or entirely by the power generated by the respective sensor.

BACKGROUND

Power consumption is an issue relative to electrochemical sensors. Conventional potentiostats have to supply current to the sensor even if the sensor would be capable of generating its own current when operated in a simple two electrode load resistor circuit.

Conventional potentiostats actively force current through the counter/working electrode circuit so as to maintain a desired potential difference between working and reference electrodes. Consumable anode oxygen sensors based on metals such as zinc or tin suffer from issues due to the sensing electrodes being driven to a potential where they can evolve hydrogen. The effect becomes worse at elevated temperatures. Hydrogen evolution on the sensing electrode also results in a background current, additional consumption of the anode, and issues relating to venting the evolved hydrogen from the sensor.

DETAILED DESCRIPTION

Figure 1:
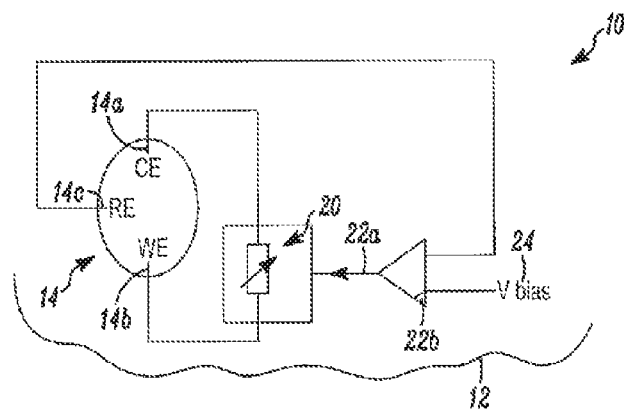
FIG. 1 is a schematic diagram of one embodiment of a dynamic embodiment hereof.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In one aspect hereof, power consumption associated with detectors which include electrochemical sensors, particularly gas sensors, can advantageously be reduced. Electrochemical embodiments hereof can include either two, three, or more electrodes.

Use can be made of the fact that electrochemical sensors can generate their own power. Some of this power can be used to power associated circuitry. An electronically variable load resistance, for example, a transistor or a diode, whose value is actively or passively adjusted, can be used to maintain the desired potential between working and reference electrodes. This circuit can use power generated by the respective sensor. It advantageously does not actively apply power to the sensor. It receives its power requirement, so as to adjust the electronically variable resistance device, from the sensor it is regulating. In some embodiments, a feedback amplifier can also be powered, at least in part from power generated by the respective sensor, or from a separate source.

Since in embodiments hereof, the driving electrical energy comes from the sensor itself, the maximum voltage and current are determined by the sensor. Specifically this means that it is not possible to operate the sensor at a bias voltage which is outside the range delimited by zero (i.e., short circuit) and the open circuit voltage of the sensor. Also, as the open circuit voltage is approached the available current is decreased.

In an alternate embodiment, a 'passive' system comprising a component such as a diode can be used to produce a voltage drop across a sensor such as an oxygen sensor. For example, in some embodiments, a 'passive' system can include a system that is not active and does not include a transistor. In this configuration, the voltage drop is preferably sufficient to prevent hydrogen evolution without causing excessive loss of activity, over the normal operating current range of the sensor.

The above approach can be applied to self-diagnostic circuits where it is desirable to deliberately reduce the rate of the electrode reaction by operation at a different bias voltage to that normally used. For example, for two electrode consumable lead anode oxygen sensors, useful diagnostics can be obtained by varying the sensor bias voltage so as to reduce the electrode activity. Normally this would require the use of an active potentiostatic circuit however this requires power consumption and so is undesirable as oxygen sensors normally operate into a load resistor and require no external power. With the present methods and circuits, such sensors can be potentiostatically controlled without significantly increasing power consumption.

One possible, exemplary, implementation of an electrochemical detector 10 is illustrated in FIG. 1. In FIG. 1, the detector 10 includes a housing 12 which carries an electrochemical gas sensor 14. Sensor 14 includes a counter electrode 14a, a working electrode 14b and a reference electrode 14c.

Component 20 is some form of electronically adjustable variable resistance. This could be, for example, a transistor (bipolar or field effect), or an electronically adjustable potentiometer. For example, a digital potentiometer such as the Analog Devices AD5258 or similar device, or an electronically adjustable mechanical variable resistor, or any other means of generating a device whose electrical resistance can be adjusted electronically.

Component 22, includes a digital or analog comparator. It measures the voltage developed between the reference electrode, 14c, and working electrode, 14b, and outputs a signal on line 22a to adjust the resistance of component 20. Component 22 adjusts the resistance of component 20 to ensure that the bias voltage between the working and reference electrodes 14b, c is held equal to the desired bias voltage, 24. In many applications, the bias voltage 24 is zero as would be understood by those of skill in the art. Component 22 could be implemented as an analogue device such as an operational amplifier. Alternately, a digital device such as a microcontroller indicated at 22b can be used.

In practice, the required bias voltage 24 could be a variable depending on the sensor current. For example the sensor 14 could be made to operate in a regime somewhere between that of an open circuit potentiometric device and a fully potentiostatically controlled amperometric device. As with conventional potentiostats, the circuit of FIG. 1 can be used in a 2-electrode mode by connecting the 'reference' and 'counter' terminals, corresponding to electrodes 14a, 14c, together and can also readily be expanded to include additional working electrodes.

Circuitry for measuring the current generated by the sensor 14 can also be provided. The use of a current follower is not desirable, as it is an active current sink and therefore needs to supply a current equal to that being measured. Possible circuits to measure the current include, but are not limited to: a fixed resistor in series with either the working or counter electrode with a means of measuring the voltage developed across it, or, if the resistance of the variable resistance device, 20, is known (as could be the case if it is for example an electronically controllable mechanical or solid state potentiometer), or if its resistance can be calculated based on the voltages applied to it, as could be the case for example with a field effect transistor, then the current flowing through device 20 can be calculated from the voltage developed across it.

If the variable resistance device 20 is a bipolar transistor then its current can be calculated from measurements of either the base current or base voltage if its characteristics are well defined. In some cases (particularly where the variable resistance device 20 is a bipolar or field effect transistor) a second matched device of the same type as the variable resistance device 20 may be required to compensate for temperature effects. Alternately, external temperature compensation circuits can be used. For some applications—for example 'bias boards' used to maintain sensors under correct bias conditions while in storage, it may not be necessary to measure the sensor current. However, such circuits would still benefit from longer battery life.

Figure 2:
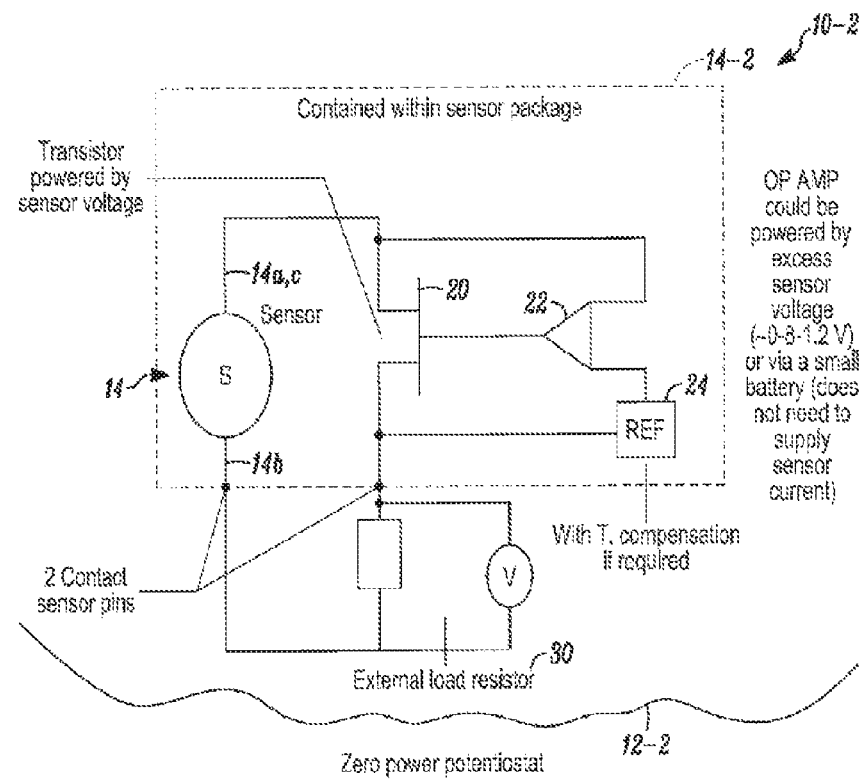
FIG. 2 is a schematic diagram of another embodiment hereof.

FIG. 2 illustrates an implementation of a detector 10-2 configured with a "drop in" replacement 14-2 for existing 2-electrode consumable anode oxygen sensors. Elements in FIG. 2 corresponding to previously discussed elements of FIG. 1 have been assigned the same identification numerals and need not be discussed again. The current measuring component 30 (typically a resistor or sometimes a current follower) is external to the sensor package 14-2. A reference generating element 24, which could be temperature compensated, is coupled to comparator 22.

As will be understood by those of skill in the art, in FIG. 2, the power supply for the op amp 22 is not explicitly shown—it may be provided by a small button cell or similar battery since the power requirement for the op amp is small. For example if an Analog Devices Model AD8500 low power, low voltage op amp is used, to power op amp 22 continuously for 5 years at 1 microamp only 44 milliamp hours are required. This can be achieved by a single lithium button cell whose diameter (12.5 mm) would fit conveniently within a City Technology 4-Series sensor housing and only take up 2.5 mm of height. Op amps are now available that can operate on a single 1.5V cell, allowing possibly further reductions in cell size.

In comparison, operating the oxygen sensor 14 with a conventional powered potentiostatic circuit, with nominal sensor current of 100 uA for 5 years would require on the order of 4.4 amp hours. This requires a battery considerably larger than a 4-series sensor package.

Figure 3:
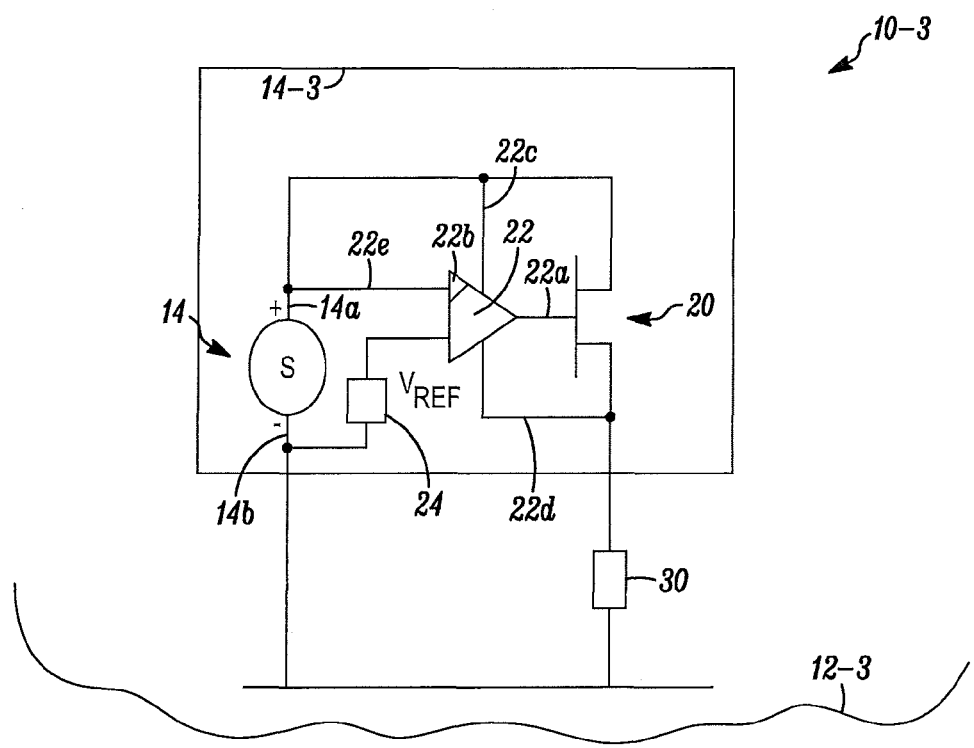
FIG. 3 is a schematic diagram of yet another embodiment hereof.

Another implementation 10-3 is illustrated in FIG. 3. In the embodiment 10-3, energy from the sensor 14 is diverted to power the resistance adjusting operational amplifier 22. A housing 12-3 carries the detector 10-3.

The Sensor 14 and control circuitry 22a are contained within housing 14-3 which has a 2 pin connection and can be manufactured as a mechanical and electrical drop in replacement for existing 2 pin consumable anode sensors as discussed above relative to FIG. 2. An impedance element, such as the load resistor 30, an active impedance element, such as an operational amplifier current follower circuit, or any other suitable current measuring circuit, is external to the housing and integrated sensor 14-3, as is currently normal practice for oxygen sensors. Voltage reference 24 defines the potential to be maintained across the sensor 14 to avoid hydrogen evolution or activity issues and may be designed to vary with temperature if required. Pass transistor 20 is used to generate the required voltage drop across the sensor 14 and may be a zero voltage threshold mosfet or similar.

Operational amplifier 22 drives pass transistor 20 to maintain the desired voltage across the sensor 14. As discussed above, op amp 22 may be an integrated device or may be built from discrete, zero threshold mosfets or similar components, without departing from the spirit and scope hereof. The op amp 22 may be powered directly from the excess voltage across the sensor, in which case its positive supply 22c is connected to the positive terminal of the sensor at 14a and its negative supply 22d is preferably connected to the output pin 14b as shown so that current flowing through the op amp 22 is still measured by the external circuit 30 since it is the total current from the sensor that needs to be measured.

Alternatively, the op amp 22 could be powered from a separate electrode in the sensor, or an internal battery, in which case the negative supply 22d from the op amp 22 should instead be connected directly to the negative pin, at 14b, of the sensor 14 so that the current which flows through the op amp 22 is not added to the measured output current. Such circuitry can be adapted to three electrode systems, which have a reference electrode in addition to the usual sensing and counter electrodes, as would be understood by those of skill in the art, by connecting input 22e of the op amp 22 in FIG. 3 to the reference electrode 14c rather than to the sensing electrode. In yet another aspect, a step up circuit could be provided to generate a suitably high power supply voltage, from a lower sensor voltage, to energize the op amp 22.

As discussed above relative to FIGS. 1-3, an active circuit can be provided to maintain a constant voltage configuration. Alternate embodiments provide a sensor configuration which incorporates one or more passive components to provide a temperature compensated, self-powered circuit with only two terminals in series with the sensor. It is recognized that zinc anode sensors, for example, will exhibit increased background current with increased temperature.

Alternately, as noted above, a diode can be coupled across a sensor to provide a relatively constant voltage drop over a range of currents. Thermistors can be added in series and/or in parallel with a diode to implement temperature compensation.

Figure 4:
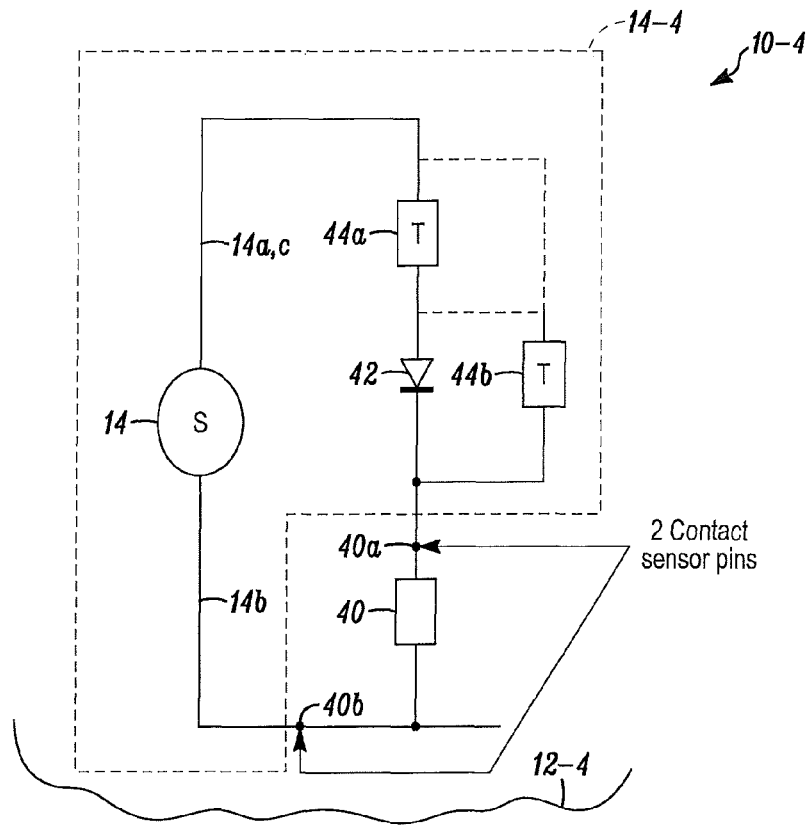
FIG. 4 is a schematic diagram of a static embodiment.

FIG. 4 illustrates a temperature compensated, static embodiment of a gas detector 10-4. In embodiment 10-4, sensor 14 is configured for two terminal operations as discussed above. Package 14-4 removably carried in housing 12-4, carries two contact pins 40a, b which couple the sensor contact 14b to load resistor 40, via contact 40b. Contact 40a couples load resistor 40 to diode 42.

Diode 42 provides a substantially constant, predetermined, voltage drop across sensor 14. As discussed above, diode 42 is powered with a current generated by sensor 14. Elements 44a, b which could be thermistors provide temperature compensation for the diode 42.

With respect to the embodiment of FIG. 4 hereof, if thermistor 44b with a resistance which increases with temperature is coupled in parallel with diode 42, then at low temperatures it can effectively create a low resistance path in parallel, pulling down the voltage drop. In extreme cases it may be possible to short out the diode almost completely if the background current at zero bias at low temperature is acceptably low.

The thermistor can be chosen such that at high temperatures its resistance is high compared with the diode so that the diode alone defines the bias voltage. In addition, or instead of this, a thermistor with a resistance which increases with temperature can be put in series with the diode. The thermistor can be selected such that at low temperatures the voltage drop across it is low so that the diode alone defines the bias voltage whereas with increasing temperature the bias voltage is increased.

It should be noted that the addition of thermistors in series, such as 44a, and/or parallel such as 44b with the diode 42 will compromise the performance of the circuit to some extent as thermistors have a linear I/V characteristic rather than a forward voltage which is almost constant with current. However this may be acceptable if, for example, the required bias voltage at low temperature is sufficiently low that the diode can be almost completely shorted out, or if at high temperatures the speed of response of the sensor is sufficiently fast that the presence of an additional series resistance (which will slow down the response) is not an issue.

Figure 5:
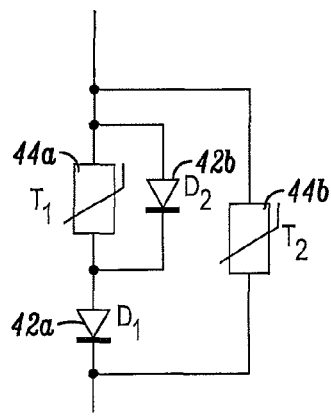
FIG. 5 is a schematic diagram of another static embodiment.

An alternate passive-type temperature compensated circuit, usable in the detector 10-4 embodiment is illustrated in FIG. 5 which includes two diodes 42a, 42b and two thermistors 44a, 42b. Both thermistors are PTC types, i.e. their resistance increases with increasing temperature.

The circuit of FIG. 5 could preferably used with a zinc-type version of sensor 14. The components may be chosen so that at 'ambient' temperatures and below the resistance of thermistor T1 is sufficiently low that it effectively shorts out diode D2. Thus for moderate to low temperatures the equivalent circuit is that of D1 and T2 in parallel. T2 is chosen such that at 'moderate' temperatures (e.g. 20C) its resistance is sufficiently large that the circuit behaves as diode D1 alone.

At low temperatures (e.g. −20 C.) the resistance of T2 is intended to short out the diode D1, with the result that the bias voltage drops towards zero. The advantage of this is that the impedance of the circuit is low, minimizing the RC time constant formed with the sensor capacitance, minimizing any degradation of speed of response which will already be slow due to the low temperature.

In summary, unwanted voltage generated by the sensor itself is dropped across a suitable component. In one disclosed embodiment, this may be performed passively by using, for example, one or more diodes. The diodes could be temperature compensated. Alternatively an active component may be used such as a transistor or any other component whose IN characteristics can be controlled/adjusted. In this case it is possible to actively adjust the voltage dropped across the component. This can be used to ensure a consistent voltage drop over a wide sensor operating current.

For example a diode such as a 1n4148 will generate a self bias voltage of 500 millivolts at a sensor current of 85 microamps, dropping to 300 millivolts at a baseline sensor current of 3 microamps. A better performance can be achieved when using a field effect transistor connected as a diode. For example three PN4117A field effect transistors in parallel, with their source and drain terminals connected together and used as a diode cathode, and their gates connected together and used as a diode anode, results in a very low leakage diode which generates a voltage of 700 millivolts at 75 microamps dropping to 370 millivolts at a baseline sensor current of 1 nanoamp. The performance of such circuitry is illustrated in FIG. 6, discussed below.

Compensation can be provided in various circuits for temperature variations of the transistor. Feedback can be in the form of simply maintaining a constant voltage across the transistor itself, a constant voltage across the transistor and a series measuring resistor, or could be made to vary in a controlled way to compensate for non-idealities in the sensor—for example to change the bias voltage with temperature. In a three electrode system the voltage drop can be adjusted based on the voltage measured on a reference electrode as in a conventional three electrode potentiostat circuit. Electrode materials can include tin, zinc, antimony and bismuth all without limitation.

Figure 6:
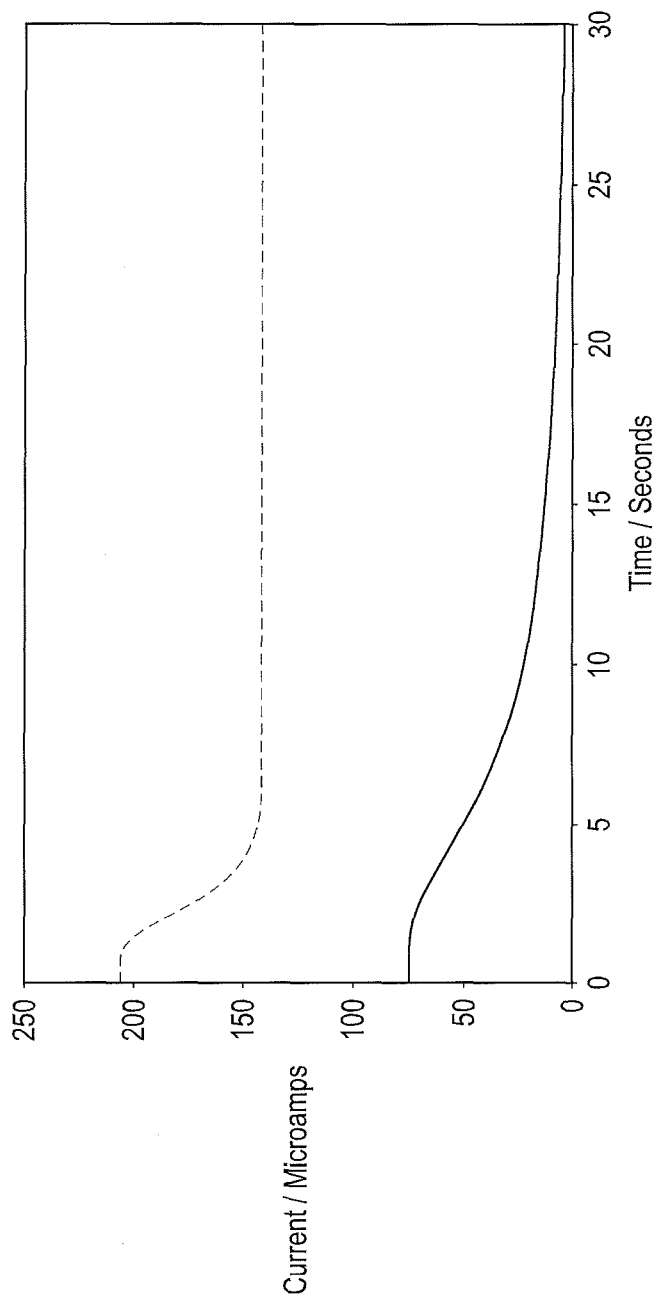
FIG. 6 is a graph illustrating sensor performance with and without circuitry as disclosed herein.

FIG. 6 illustrates the behavior of a zinc anode based sensor with and without application of the circuitry and methods hereof. The sensor construction is based on a commercially available City Technology 4OX2L oxygen sensor but with a zinc anode in place of the usual lead anode. The zinc anode was formed from 5 grams of 1 mm diameter zinc wire (99.99% purity) soldered at one end to a nickel current collector with the nickel and solder joint encapsulated in epoxy to isolate these from the electrolyte to prevent electrochemical cells forming between these and the anode. The electrolyte was a conventional aqueous 4M Potassium Acetate solution, and the sensing electrode is a 5% Platinum on graphite gas diffusion electrode as used in the 4OX2L sensor.

The use of a relatively thick zinc wire and hence low surface area for the anode minimizes self-discharge effects and hydrogen evolution due to local cells on the zinc surface without compromising sensor performance. The theoretical lifetime of the zinc anode sensor in air is approximately 5 years compared to 2 years for a lead anode sensor of the same physical size and current output due to the higher energy density of zinc.

FIG. 6 illustrates an exemplary output signal from the sensor (dashed line) when connected to a 100 ohm load resistor (the conventional method of operating the 4OX2L sensor). Alternatively the output signal from the sensor, (solid line) is illustrated with the circuit incorporating three PN4117A Field effect transistors in parallel, configured as diodes, with drain and source terminals connected together.

Initially the sensor is exposed to synthetic air (21% oxygen in nitrogen). At time=1 second the sensor is exposed to 100% nitrogen and the sensor signal drops towards zero. It can be seen that there is a large parasitic current due to hydrogen evolution on the sensor with a simple load resistor. This is almost completely removed when the diodes are added to the system. The steady state signal in nitrogen, which should be zero for an ideal sensor, is 135 microamps without the diodes, and 1 nanoamp with the diodes, measured after 5 minutes in nitrogen.

It should be noted that although the signal without the diodes appears to initially respond to nitrogen more quickly, there is a prolonged slow downward drift of tens of microamps in the signal in nitrogen, so that simply subtracting a constant background signal is not an option. This background signal is also strongly temperature dependent.

It is to be understood that, although some embodiments described above, have been described with respect to oxygen sensors, embodiments disclosed herein are not so limited. For example, some embodiments disclosed herein can be used in connection with carbon monoxide (CO) sensors. For example, in accordance with the above, the hydrogen cross-sensitivity of a carbon monoxide sensor can be reduced by biasing the carbon monoxide sensor to slightly less than an active potential as compared to the active potential under normal operating conditions.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A method of controlling an electrochemical sensor comprising:
   operating the sensor and generating a sensor voltage wherein one of a substantially fixed load resistance or an electronically variable load resistance is coupled to the sensor;
   adjusting the resistance so as to maintain a selected sensor voltage, wherein electrical energy from the sensor is coupled to the fixed load resistance or the variable load resistance;
   varying the sensor voltage to reduce electrode activity; and
   obtaining diagnostic information for at least one electrode in response to varying the sensor voltage.

2. A method as in claim 1 which includes providing a feedback element with an output signal, coupling the output signal to the load resistance, and, adjusting the resistance using the output signal.

3. A method as in claim 1 which includes maintaining the selected voltage between first and second electrodes of the sensor.

4. A method as in claim 1, wherein the sensor comprises an oxygen sensor comprising two electrodes, and wherein obtaining the diagnostic information comprises obtaining diagnostic information for the two electrodes.

5. A method as in claim 1, wherein the sensor comprises a plurality of electrodes, and wherein obtaining the diagnostic information comprises obtaining diagnostic information for the plurality of electrodes.

6. An apparatus comprising:
   an electrochemical sensor, carried in a housing with two terminals carried on the housing coupled to respective sensor electrodes, and sensor output voltage establishing circuitry carried in the housing, coupled to and only powered by the sensor.

7. An apparatus as in claim 6, where circuitry comprises an electronically variable load resistance coupled to the sensor to maintain a selected sensor voltage.

8. An apparatus as in claim 6 which includes an electrical load, releasably coupled to the sensor, wherein a voltage across the load is indicative of a gas concentration at the sensor.

9. The apparatus as in claim 6, where the sensor output voltage establishing circuitry comprises an electronic component comprising a diode to produce a voltage drop across the sensor, where the voltage drop is sufficient to prevent hydrogen evolution without causing loss of activity over a normal operating current range of the sensor.

10. The apparatus as in claim 6, wherein the electrochemical sensor comprises a two electrode consumable anode oxygen sensor.

11. The apparatus as in claim 6, wherein the electrochemical sensor includes at least first and second electrodes, wherein the sensor output voltage establishing circuitry is configured to maintain a selected voltage between the at least first and second electrodes.

12. An electrochemical detector comprising:
   an electrochemical sensor, wherein the electrochemical sensor comprises an oxygen sensor;
   at least one of an active voltage control circuit comprising a closed loop control system Which includes an electronically variable load resistance coupled to the sensor to maintain a selected sensor voltage, or, an electronic component comprising a diode to produce a voltage drop across the sensor, where the voltage drop is sufficient to prevent hydrogen evolution without causing loss of activity over a normal operating current range of the sensor, and wherein power is obtained, at least in part, from the sensor; and
   a first housing which carries at least the electrochemical sensor and a second housing which releasably receives the first housing, wherein the electrochemical sensor is coupled to an impedance element.

13. A detector as in claim 12 wherein the sensor comprises a two electrode consumable anode oxygen sensor.

14. A detector as in claim 13 where the consumable anode is selected from a class that includes at least one of a zinc or tin consumable anode.

15. A detector as in claim 14 where the sensor includes at least first and second electrodes and where the selected voltage is maintained therebetween.

16. A detector as in claim 12 where the first housing carries at least two contacts on an external surface of the housing and wherein the contacts electrically engage the impedance element when the first housing is positioned in the second housing.

17. A detector as in claim 16 where the contacts releasably engage the conductors coupled to the impedance element.

18. A detector as in claim 17 where the sensor comprises an oxygen sensor.

* * * * *